United States Patent

Hasenzahl et al.

[11] Patent Number: 6,054,112
[45] Date of Patent: *Apr. 25, 2000

[54] PROCESS FOR THE PREPARATION OF TITANIUM CONTAINING MOLECULAR SIEVES

[75] Inventors: Steffen Hasenzahl; Georg Thiele, both of Hanau, Germany

[73] Assignee: Degussa-Huls AG, Frankfurt, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/957,442

[22] Filed: Oct. 24, 1997

Related U.S. Application Data

[60] Provisional application No. 60/030,625, Nov. 8, 1996.

[30] Foreign Application Priority Data

Oct. 25, 1996 [DE] Germany ............... 196 44 348

[51] Int. Cl.⁷ ............... C01B 37/00; C01B 33/20
[52] U.S. Cl. ............... 423/705; 423/707; 423/713; 423/DIG. 22; 423/DIG. 27; 423/DIG. 29; 423/326
[58] Field of Search ............... 423/702, 705, 423/713, DIG. 22, DIG. 27, DIG. 29, 326, 707; 502/77, 242

[56] References Cited

U.S. PATENT DOCUMENTS

| | | | |
|---|---|---|---|
| 4,410,301 | 10/1983 | Westmoreland . | |
| 4,410,501 | 10/1983 | Taramasso et al. | 423/705 |
| 4,831,201 | 5/1989 | Giusti et al. | 423/326 |
| 4,831,202 | 5/1989 | Giusti et al. | 423/713 |
| 5,003,125 | 3/1991 | Giusti et al. | 423/326 |
| 5,082,641 | 1/1992 | Popa et al. . | |
| 5,246,690 | 9/1993 | Bellussi et al. | 423/DIG. 22 |
| 5,290,533 | 3/1994 | Bellussi et al. | 423/DIG. 22 |
| 5,474,754 | 12/1995 | Saxton et al. | 423/713 |
| 5,688,484 | 11/1997 | Saxton et al. | 423/DIG. 22 |

FOREIGN PATENT DOCUMENTS

| | | |
|---|---|---|
| 1001038A7 | 6/1989 | Belgium . |
| 0 659 685 A1 | 12/1994 | European Pat. Off. . |

OTHER PUBLICATIONS

G. Zhang, J. Sterte and B. Schoeman, Preparation of Colloidal Suspensions of Discrete TS–1 Crystals, American Chemical Society, pp. 210–217, Jan. 1997.

J. Sudhakar Reddy and Rajivi Kumar, Synthesis, Characterization, and Catalytic Properties of a Titanium Silicate, TS–2, with MEL Structure, Journal of Catalysis, 1991, pp. 440–446 (no month).

*Primary Examiner*—Elizabeth Wood
*Assistant Examiner*—David Sample
*Attorney, Agent, or Firm*—Pillsbury Madison & Sutro LLP

[57] ABSTRACT

Titanium-containing molecular sieves are prepared by adding an aqueous template solution to a mixture of tetraalkyl orthosilicate and tetraalkyl orthotitanate, crystallizing the reaction mixture in an autoclave and separating the solid obtained optionally, the solid is washed and calcined. The titanium-containing molecular sieves can be used as catalysts, inter alia in the epoxidation of olefins.

8 Claims, No Drawings

6,054,112

PROCESS FOR THE PREPARATION OF TITANIUM CONTAINING MOLECULAR SIEVES

This application is based on application No. 196 44 348.2 filed in Germany on Oct. 25, 1996 and on U.S. application Ser. No. 60/030625 filed on Nov. 8, 1996, the content of which is incorporated hereinto by reference.

BACKGROUND OF THE INVENTION

1. Field of the Invention

The present invention relates to a process for the preparation of crystalline titanium-containing molecular sieves of the composition $(SiO_2)_{1-x}(TiO_2)x$, $(0,0001 \leq x \leq 0,03)$ from a tetraalkyl orthosilicate, a tetraalkyl orthotitanate and an aqueous template solution.

2. Prior Art

Crystalline molecular sieves of the composition $(SiO_2)_{1-x}(TiO_2)_x$ are known in which titanium atoms replace some of the silicon atoms in the crystal lattice. These are specifically titanium silicalite-1 of the MFI crystal structure (DE 30 47 798), titanium silicalite-2 of the MEL crystal structure (BE 1 001 038 and J. S. Reddy, R. Kumar, P. Ratnasamy, Appl. Catal. 58 (1990) L1, titanium beta-zeolite of the BEA crystal structure (M. A. Camblor, A. Corma, A. Martines, I. Perez-Pariente, J. Chem. Soc., Chem. Commun. 1992, 589 and EP 659 685) and TS-48 with the crystal structure of zeolite ZSM48 (D. P. Serrano, H. X. Li, M. E. Davis, J. Chem. Soc., Chem. Commun. 1992, 745).

The known crystalline titanium-containing molecular sieves are used as catalysts, especially for oxidation reactions with hydrogen peroxide or organic hydroperoxides. Examples are the use of titanium silicalite-1 as a catalyst for the reaction of olefins with hydrogen peroxide to give epoxides (EP 100 119), the reaction of aromatics with hydrogen peroxide to give hydroxyaromatics (DE 31 35 559), the reaction of aliphatic hydrocarbons with hydrogen peroxide to give alcohols and ketones (EP 376 453) and the reaction of cyclohexanone with hydrogen peroxide and ammonia to give cyclohexanone oxime (EP 208 311). Examples for the use of titanium silicalite-2 are the hydroxylation of phenol (J. S. Reddy, S. Sivasanker, P. Ratnasamy, J. Mol. Catal. 71 (1992) 373) and the reaction of cyclohexanone with hydrogen peroxide and ammonia to give cyclohexanone oxime (J. S. Reddy, S. Sivasanker, P. Ratnasamy, J. Mol. Catal. 71 (1992) 383). Titanium beta-zeolite can be used as a catalyst for the reaction of olefins with hydrogen peroxide or organic hydroperoxides to give epoxides (A. Corma, P. Steve, A. Martines, S. Valencia, J. Catal. 152 (1995) 18 and EP 659 685).

The known crystalline titanium-containing molecular sieves are prepared by hydrothermal synthesis. In the first step a tetraalkyl orthosilicate as a silicon source and a tetraalkyl orthotitanate as a titanium source are hydrolyzed with a tetrasubstituted ammonium hydroxide as a basic and structure-determining component (template), in the presence of water, the alcohol formed from the hydrolysis of the tetraalkyl orthosilicate and the tetraalkyl orthotitanate is then distilled off, the resulting sol is crystallized at a temperature above 100° C. under pressure and the solid formed is separated off, washed, dried and calcined at a temperature above 300° C.

It is further known to prepare titanium silicalite-1 from tetraethyl orthosilicate and tetraethyl orthotitanate. Here the synthetic sol is prepared by hydrolyzing a mixture of tetraethyl orthosilicate and tetraethyl orthotitanate by the addition of aqueous tetrapropylammonium hydroxide solution. The alcohol formed is then distilled off and the resulting sol is crystallized at a temperature of 175° C. under autogenous pressure (U.S. Pat. No. 4,410,501).

It is known from EP 543 247 that the tetrapropylammonium hydroxide can be replaced with a combination of tetra-npropylammonium bromide and ammonia in the synthesis of titanium silicalite-1.

Titanium silicalite-2 (MEL structure) and titanium betazeolite (BEA structure) are prepared using tetra-nbutylammonium hydroxide and tetraethylammonium hydroxide, respectively.

According to B. Notari, Stud. Surf. Sci. Catal. 67 (1991) 243, the hydrolysis of the mixture of the silicon and titanium components with the aqueous solution of the basic template is a critical step which is liable to cause problems. Thus, the formation of a titanium- containing precipitate in the preparation of the sol must be avoided under all circumstances; otherwise the titanium is not available for the crystallization and materials of lower catalytic activity, which are moreover contaminated with titanium dioxide, are formed.

According to A. J. H. P. van der Pol et al., Appl. Catal. A. 92 (1992) 93–111, the formation of a sparingly soluble precipitate in the preparation of a synthetic sol for the synthesis of titanium silicalite can be avoided if the mixture of tetraethyl orthosilicate and tetraethyl orthotitanate is first cooled to 0° C. and the aqueous tetrapropylammonium hydroxide solution, also precooled to 0° C., is metered in dropwise, with stirring. The same applies to the synthesis of titanium silicalite-2 and titanium beta-zeolite.

The known processes have the disadvantage that the preparation of the synthetic sol is expensive and liable to cause problems. Thus, the metering of the aqueous template solution takes several hours and the temperature and rate of addition have to be precisely maintained. Also, an additional working step is required for the distillation of the alcohol formed in the hydrolysis.

SUMMARY OF THE INVENTION

The object of the invention is to develop a process for the synthesis of titanium-containing molecular sieves which is characterized in particular by an easy preparation of the sol.

The invention provides a process for the preparation of crystalline titanium-containing molecular sieves of the composition $(SiO_2)_{1-x}(TiO_2)_x$, $(0,000 \leq x \leq 0,03)$ characterized in that an aqueous template solution is added to a mixture of a tetraalkyl orthosilicate and a tetraalkyl orthotitanate, the resulting reaction mixture is placed in an autoclave, without distillation of the alcohols formed in the hydrolysis, and crystallized at a temperature above 100° C., preferably at 170 to 190° C., under autogenous pressure and the solid obtained is then separated from the reaction mixture in known manner, optionally washed and calcined at 400 to 1000° C.

The tetraalkyl ortho-silicates and tetraalkyl ortho-titanates used for the preparation of titanium-containing molecular sieves are preferably those in which alkyl is methyl, ethyl, propyl or butyl, preferably ethyl.

Templates which can be used are compounds which, by being taken up into the crystal lattice of the product during the crystallization, determine the crystal structure of the products formed. Suitable examples are amines having one or more amino groups, amino alcohols or tetrasubstituted ammonium compounds. It is preferable to use tetraalkylammonium compounds like tetraalkyl-ammonium hydroxide, especially tetra-n-propylammonium hydroxide, for the preparation of titanium silicalite-1 (MFI structure), tetra-n-butylammonium hydroxide for the preparation of titanium silicalite-2 (MEL structure) and tetraethylammonium hydroxide for the preparation of titanium beta-zeolite (BEA crystal structure). The template compounds are preferably used as aqueous solutions.

The pH of the synthetic sol required for the synthesis, namely>9, preferably >11, can be achieved either by using adequate amounts of a template giving a basic reaction, or by adding a base such as ammonia or an organic amine, for example methylamine or 1,6-hexamethylenediamine.

The proportions of the starting materials can be chosen within the limits of the following molar ratios: $(RQ)_4Si/(RO)_4Ti=5-1000$, preferably 35–60 template/$(RO)_4Si=$ 0.04–2.0, preferably 0.2–0.4 OH/$(RO)_4Si=0.04-2.0$, preferably 0.2–0.4 $H_2O/(RO)_4Si=5-200$, preferably 15–30 R being an alkyl group from the group comprising methyl, ethyl, propyl and butyl.

The temperature at which the synthetic sol is prepared can be chosen within wide limits. The preparation is preferably carried out at room temperature. The rate of addition of the aqueous template solution can also be varied within wide limits. Because of the economics of the synthesis, however, the addition is preferably effected within a few minutes.

Then, optionally after an additional aging time, the synthetic gel is crystallized at a temperature above 100° C., preferably at 170 to 190° C., it being possible for the crystallization time to be between 0.5 h and 14 days, depending on the temperature used. A crystallization time of 24 h is generally sufficient. The crystals are separated from the mother liquor by filtration, centrifugation or recantation and washed with a suitable washing liquid, preferably water. The crystals are then optionally dried and calcined at a temperature between 400 and 1000° C., preferably between 500 and 750° C., to remove the template.

If desired, to remove any alkali metal ions present, the calcined product can be treated once again with a solution of an ammonium salt, preferably an aqueous solution of ammonium nitrate or ammonium acetate, or with a strong mineral acid, preferably an aqueous solution of sulphuric acid, hydrochloric acid or nitric acid, and calcined again.

After the alcohol has first been distilled off, all or some of the mother liquor remaining after the crystallization can be recycled into the process according to the invention, being used instead of water in the preparation of the synthetic gel. The amount of template required for the preparation of the synthetic gel is then reduced by the amount remaining in the mother liquor after the crystallization.

The process according to the invention makes it possible to prepare crystalline titanium-containing molecular sieves which are particularly suitable as catalysts for oxidation reactions with hydrogen peroxide or organic hydroproxides.

The titanium-containing molecular sieves according to the invention can preferably be used in the following reactions:

1. The epoxidation of olefins with hydrogen peroxide, examples of possible olefins being propene, but-1ene, cis- and trans-but-2-ene, pent-1-ene, hex-1-ene, oct-1-ene, dec-1-ene, dodec-1 -ene, isobutene, isoamylene, butadiene, isoprene, cyclopentene, cyclohexene, cyclooctene, allyl chloride, allyl alcohol or allyl acetate.
2. The hydroxylation of aromatics with hydrogen peroxide, examples being benzene, toluene, xylenes, phenol or anisole.
3. The ammoximation of carbonyl compounds with hydrogen peroxide and ammonia to give the corresponding oximes, examples of possible carbonyl compounds being acetone, butan-2-one, cyclohexanone, cyclododecanone, benzaldehyde or acetophenone.
4. The oxidation of secondary alcohols with hydrogen peroxide to give ketones.

The crystalline titanium-containing molecular sieves according to the invention are obtained in powder form. For their application as oxidation catalysts they can be converted to a form suitable for application, for example, microgranules, spheres, tablets, solid cylinders, hollow cylinders or honeycomb objects, by a choice of known processes for the shaping of powder catalysts, for example, granulation, spray drying, spray granulation or extrusion.

The titanium-containing molecular sieve prepared according to the invention can be used as a catalyst in oxidation reactions with $H_2O_2$. In particular, the titanium containing molecular sieve according to the invention can be used as a catalyst in the epoxidation of olefins, preferably in the epoxidation of propene by means of $H_2O_2$.

The process according to the invention has the advantage that the sol preparation step, in particular, is simpler and less liable to cause problems than in the known processes.

DETAILED DESCRIPTION OF PREFERRED EMBODIMENTS OF THE INVENTION

EXAMPLES

Example 1 (According to the Invention)

91.7 g of tetraethyl orthosilicate are placed in a polyethylene beaker and covered with argon. 2.88 g of tetraethyl orthotitanate are then added dropwise, with stirring. The reaction mixture is heated to 35° C. and stirred for half an hour at this temperature. It is then allowed to cool to room temperature and a mixture of 80.5 g of tetraethylammonium hydroxide solution (40 wt. %, aqueous solution) and 175.0 g of deionized water is added over five minutes, with stirring. The resulting milkywhite reaction mixture is placed in an autoclave and crystallized for 24 h at 175° C., with stirring.

The solid obtained is separated from the mother liquor by centrifugation, washed three times with deionized water, dried overnight at 90° C. and calcined in an air atmosphere for five hours at 500° C. The product is then treated for two hours with 1.0 N ammonium acetate solution at 80° C., washed with deionized water, dried and calcined again at 500° C.

| | |
|---|---|
| Titanium content determined by chemical analysis: | 2.9 wt. % of $TiO_2$ |
| X-ray diffraction diagram: | MFI structure |
| IR spectrum: | band at 960 cm$^{-1}$ |

Example 2 (Comparative Example)

Titanium silicalite-1 is prepared an described by A. J. H. P. van der Pol et al., Appi. Catal. A 92 (1992) 93–111. This is done by placing 208.5 g of tetraethyl orthosilicate in a polyethylene beaker and covering it with argon. 6.54 g of tetraethyl orthotitanate are then added dropwise over five minutes, with stirring. The reaction mixture is heated to 35° C. and stirred for half an hour at this temperature. It is then cooled to 0° C. and a mixture of 183,0 g of tetrapropylammonium hydroxide solution (40 wt. %) and 397.8 g of deionized water is added dropwise over five hours at this temperature. The reaction mixture is then heated to 80° C. over one hour and kept at this temperature for about four hours in order to complete the hydrolysis and distil off the ethanol formed. The volume is kept constant by the addition of deionized water. The resulting transparent sol is placed in an autoclave and crystallized for 48 h at 175° C., with stirring. The solid obtained is separated from the mother liquor by centrifugation, washed three times with deionized water, dried overnight at 90° C. and calcined in an air atmosphere for four hours at 500° C. The product is then treated for two hours with 1.0 N ammonium acetate solution at 80° C., washed with deionized water, dried and calcined again at 500° C.

| Titanium content determined by chemical analysis: | 2.4 wt. % of $TiO_2$ |
| --- | --- |
| X-ray diffraction diagram: | MFI structure |
| IR spectrum: | band at 960 $cm^{-1}$ |

Application Examples for the epoxidation of propylene hydrogen peroxide.

Example 3

1.0 g of the catalyst prepared according to Example 1 in 300 ml of methanol is placed in a thermostated laboratory autoclave with gas dispersion stirrer, at 40° C. under a propylene atmosphere, and the solvent is saturated with propylene under an excess pressure of 3 bar. 13.1 g of 30 wt. % aqueous hydrogen peroxide solution are then added all at once, with stirring, and the reaction mixture is kept at 40° C. and 3 bar, additional propylene being metered in via a pressure regulator in order to make up the quantity consumed by the reaction. Samples are taken at regular intervals on a filter and the hydrogen peroxide content of the reaction mixture is determined by redox titration with cerium(IV) sulphate solution. The plot of $\ln(C/C_O)$ against the time t, c being the measured $H_2O_2$ concentration at time t and $C_O$ being the calculated $H_2O_2$ concentration at the start of the reaction, gives a straight line. An activity coefficient k of 24.4 $min^{-1}$ is determined from the gradient of the lines by means of the relationship $dc/dt = -k \cdot c \cdot c_{cat}$, where $c_{cat}$ is the catalyst concentration in kg of catalyst per kg of reaction mixture.

Example 4

Example 3 is repeated with the catalyst prepared in Example 2. An activity coefficient of 17.2 min is determined.

What is claimed is:

1. A process for the preparation of crystalline titanium-containing molecular sieves of the composition $(SiO_2)_{1-X}(TiO_2)_X$, $(0.001 \leq x \leq 0.03)$ wherein an aqueous template solution, comprising a tetraalkylammonium hydroxide compound or a mixture of a tetraalkylammonium compound and a base, is added to a mixture of a tetraalkyl orthosilicate and a tetraalkyl orthotitanate, the resulting reaction mixture is place in an autoclave, without distillation of the alcohols formed in the hydrolysis, and crystallized at a temperature above 100° C. under autogenous pressure and the solid obtained is then separated from the reaction mixture.

2. A process according to claim 1, wherein the solid separated from the reaction mixture is washed and calcined at a temperature of 400 to 1000° C.

3. A process according to claim 1 or claim 2, wherein the template further comprises an amine having one or more amino groups, or an amino alcohol.

4. A process according to claim 1 or claim 2, wherein the template is a tetra-n-propylammonium hydroxide compound, and a titanium-containing molecular sieve with the MFI-structure is formed.

5. A process according to claim 1 or claim 2, wherein the template is a tetra-n-butyl ammonium compound and a titanium-containing molecular sieve with the MEL-structure is formed.

6. A process according to claim 1 or claim 2, wherein the tetraalkyl orthosilicate used is one in which alkyl is methyl, ethyl, propyl or butyl.

7. A process according to claim 1 or claim 2, wherein the tetraalkyl orthotitanate used is one in which alkyl is methyl, ethyl, propyl or butyl.

8. The process according to claim 1, wherein crystallization occurs at a temperature from 170 to 190° C.

* * * * *